(12) United States Patent
Chu et al.

(10) Patent No.: US 12,104,012 B2
(45) Date of Patent: Oct. 1, 2024

(54) CYCLOBUTANE-CONTAINING THERMALLY CLEAVABLE POLYMERS

(71) Applicants: Qianli Chu, Grand Forks, ND (US); Zhihan Wang, Grand Forks, ND (US)

(72) Inventors: Qianli Chu, Grand Forks, ND (US); Zhihan Wang, Grand Forks, ND (US)

(73) Assignee: UNIVERSITY OF NORTH DAKOTA, Grand Forks, ND (US)

( * ) Notice: Subject to any disclaimer, the term of this patent is extended or adjusted under 35 U.S.C. 154(b) by 702 days.

(21) Appl. No.: 17/283,878

(22) PCT Filed: Nov. 25, 2019

(86) PCT No.: PCT/US2019/062968
§ 371 (c)(1),
(2) Date: Apr. 8, 2021

(87) PCT Pub. No.: WO2020/117517
PCT Pub. Date: Jun. 11, 2020

(65) Prior Publication Data
US 2021/0363294 A1    Nov. 25, 2021

Related U.S. Application Data

(60) Provisional application No. 62/775,277, filed on Dec. 4, 2018.

(51) Int. Cl.
*C08G 63/78* (2006.01)
*C07C 51/347* (2006.01)
*C08J 11/12* (2006.01)

(52) U.S. Cl.
CPC ............ *C08G 63/78* (2013.01); *C07C 51/347* (2013.01); *C08J 11/12* (2013.01); *C08J 2367/00* (2013.01)

(58) Field of Classification Search
CPC ............ C07B 2200/09; C07C 2601/04; C07C 51/347; C07C 51/353; C07C 51/43; C07C 57/44; C07C 61/39; C08G 63/137; C08G 63/78; C08J 11/12; C08J 2367/00
See application file for complete search history.

(56) References Cited

U.S. PATENT DOCUMENTS

| | | | | | |
|---|---|---|---|---|---|
| 3,953,405 | A | * | 4/1976 | Feinauer | D06M 10/001 264/210.8 |
| 5,274,016 | A | * | 12/1993 | Berner | C08F 2/44 524/718 |
| 2019/0002387 | A1 | | 1/2019 | Chu et al. | |
| 2021/0363294 | A1 | * | 11/2021 | Chu | C08G 63/78 |

FOREIGN PATENT DOCUMENTS

| | | | |
|---|---|---|---|
| EP | 0713859 | * | 11/1995 |
| JP | 2016166315 | * | 9/2016 |

OTHER PUBLICATIONS

Mujeeb Khan et al "Transient States in [2+2] Photodimerization of Cinnamic Acid: Correlation of Solid-State NMR and X-ray Analysis", J. Am. Chem. Soc. 2008, 130, 1741-1748 (Year: 2007).*
Tao Lei et al "General and Efficient Intermolecular [2+2] Photodimerization of Chalcones and Cinnamic Acid Derivatives in Solution through Visible-Light Catalysis", Angew. Chem. Int. Ed. 2017, 56, 15407-15410 (Year: 2017).*
Xuesong Li et al "Controllable photo-switching of cinnamate-based photonic films with remarkable stability", J. Mater. Chem., 2011, 21, 17953 (Year: 2011).*
Congcong Zhu et al "Photocrosslinkable biodegradable elastomers based on cinnamate-functionalized polyesters", Acta Biomaterialia 9 (2013) 7362-7370 (Year: 2013).*
Zhihan Wang et al "Stereoregular Two-Dimensional Polymers Constructed by Topochemical Polymerization", Macromolecules 2015, 48, 2894-2900. (Year: 2015).*
International Preliminary Report on Patentability for PCT Application No. PCT/US2019/062968, Dated Jun. 17, 2021, pp. 7.
Wang et al., "Cyclobutane-1, 3-Diacid (CBDA): A Semi-Rigid Building Block Prepared by [2+2] Photocyclization for Polymeric Materials," Oct. 20, 2017 [Retrieved Jan. 20, 2020] Retrieved from Internet URL: <https://www.nature.com/articles/s41598-017-13983-z.pdf> Abstract; p. 2 Para 2; p. 3 Para 4; p. 4 Para 2; p. 5 Para 4; Fig. 2; Fig. 5.
Fernandes et al., "Photodimerisation of the alpha-polymorph of orthoethoxy-trans-cinnamic acid occurs via two-stage mechanism at 343 K yielding 100% alpla-truxillic acid." Jul. 6, 2016 Retrieved Jan. 20, 2020] Retrieved from URL: <https:///rsc.org/en/content/articlepdf/2016/ce/c6ce00809g> p. 7363 Col 1 Para 1; p. 7365 Col 1 Para 1; p. 7365 Col 2 Para 3.
Takahashi et al., A photogradable polymer: Polyhexamethylene-alpha-Truxillmide. 1971 [Retrieved Mar. 10, 2020] Retrieved from Internet URL: <https://onlinelibary.wiley.com/doi/abs/10.1002/pol.1971.110090910> p. 685 Para 1; p. 687 Para 2-4.
Amjaour et al., Scalable preparation and property investigation of a cis-cyclobutane-1, 2-dicarboxylic acid from beta-trans-cinnamic acid. Dec. 6, 2018. [Retrieved Mar. 10, 2020] Retrieved from Internet URL: <https://pubs.rsc.org/en/content.articlelanding/2019/cc/c8cc08017h#!divAbstract> p. 2 Col 2 Para 3; p. 4 col 2 Para 1; Scheme 2.

(Continued)

*Primary Examiner* — Frances Tischler
*Assistant Examiner* — Gennadiy Mesh
(74) *Attorney, Agent, or Firm* — Kinney & Lange, P. A.

(57) ABSTRACT

A polymer is made by polymerization of CBDA-4 monomers with a glycerol linker through a condensation reaction. The resulting polymer is thermally cleavable having a plurality of CBDA-4 monomers linked with the glycerol linkers, making it recyclable when heated and degraded. The resulting intermediate material can be hydrolyzed back to initial starting material for synthesizing CBDA-4 monomers.

12 Claims, 13 Drawing Sheets

(56) References Cited

OTHER PUBLICATIONS

International Search Report and Written Opinion for PCT Application PCT/US2019/62968, Dated Apr. 1, 2020, p. 9.

* cited by examiner

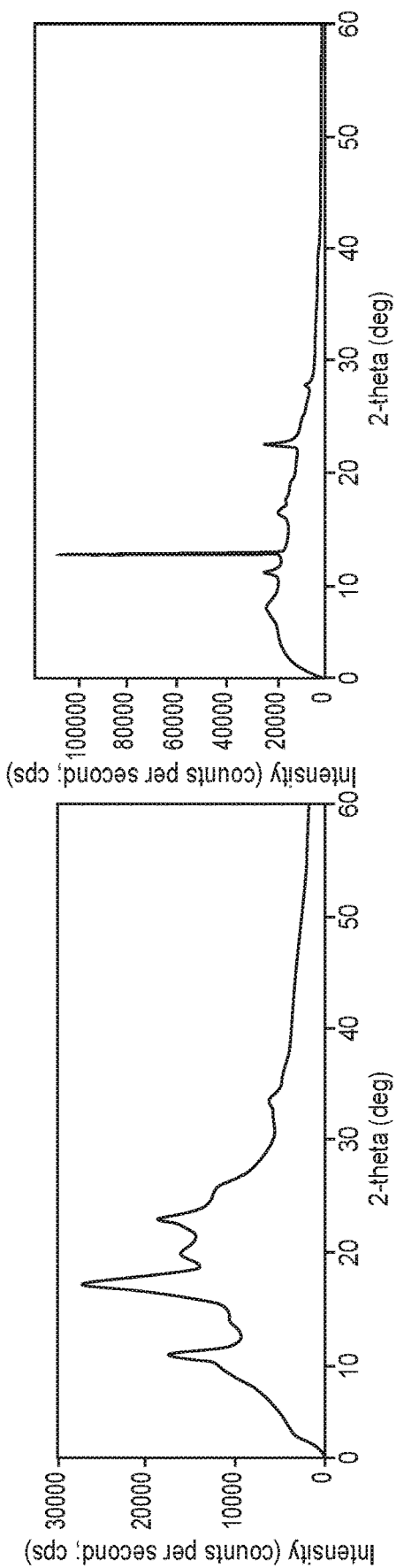
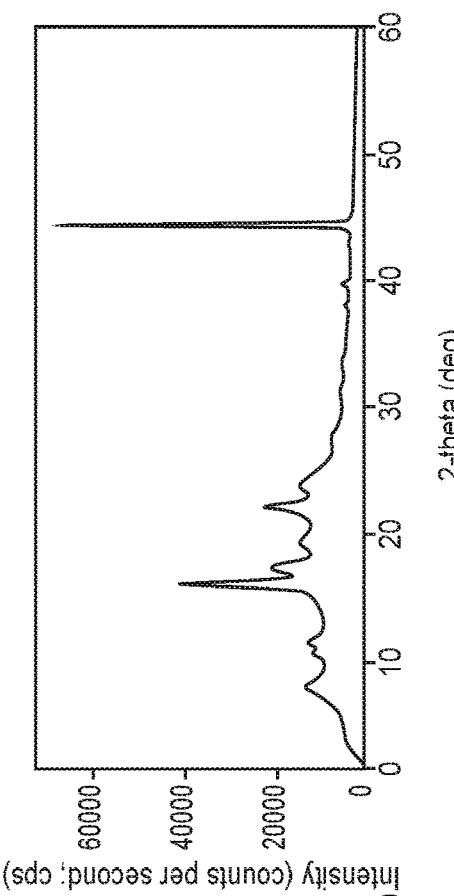
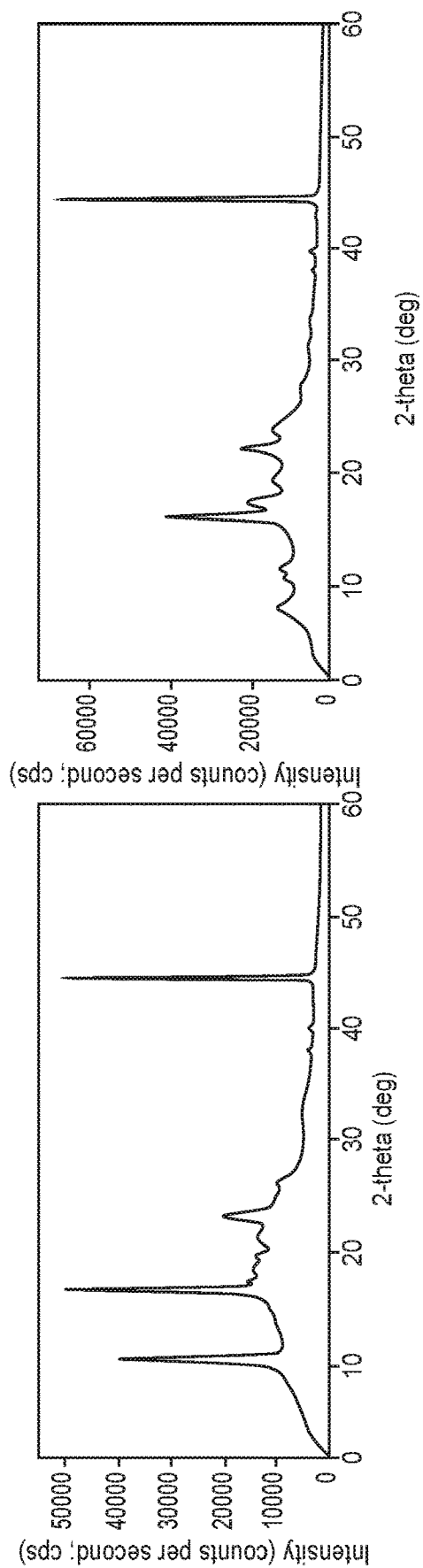
FIG. 10
FIG. 11
FIG. 12
FIG. 13

CYCLOBUTANE-CONTAINING THERMALLY CLEAVABLE POLYMERS

CROSS-REFERENCE TO RELATED APPLICATION(S)

This application claims the benefit of U.S. Provisional Application No. 62/775,277 filed Dec. 4, 2018 for "CYCLOBUTANE-CONTAINING THERMALLY CLEAVABLE POLYMERS" by Q. Chu and Z. Wang.

STATEMENT OF GOVERNMENT INTEREST

This invention was made with government support under 43700-2320-UND0019824 awarded by The National Science Foundation. The government has certain rights in the invention.

BACKGROUND

This application relates generally to polymer synthesis and specifically to thermoset thermoplastic, and elastomer synthesis.

Synthetic polymers have a broad array of applications in industry. But plastics in the global market are chiefly made from fossil-based resources. The tremendous growth of plastic consumption can cause environmental problems globally. This is due in part to the source of plastics production, which are typically non-renewable resources. Additionally, plastics can be either limited or not at all recyclable, meaning plastics may remain in nature for hundreds of years or more after disposal.

Cross-linked polymers known as thermosets have been widely used in the global market because they are easy to manufacture, and have versatility such as chemical resistance, low shrink properties, and corrosive resistance. These properties make thermosets suitable for wide applications in printed circuit boards, computer casings, coatings, polymer composites, adhesives, electrical insulation, medical equipment, aircraft and automotive applications.

However, thermosets can be difficult to dispose or recycle. They cannot be re-melted or re-molded once they are cured through cross-linking. Therefore, most thermosets are considered a non-recyclable class of plastics.

Building blocks for synthetic polymers, such as thermosets, must be stable molecules capable of producing polymer formations. Diacids are widely used in modern materials. In particular, cyclobutanedicarboxylic acids (CBDAs) and their derivatives represent promising building blocks for polymers such as thermoplastics and thermosets. In these polymers, CBDA serves as a diacid monomer or cross-linker. CBDA monomers and their derivatives can be synthesized from bio-based chemicals, such as biomass waste.

SUMMARY

In one embodiment, a method of making a polymer includes polymerizing cyclobutane diacid (CBDA) monomers with a linker through a condensation reaction and forming a thermally cleavable polymer having a plurality of CBDA monomers linked with a linker.

In second embodiment, a method of degrading a polymer includes heating the polymer to invoke degradation of cyclobutane rings and produce an intermediate compound and hydrolizing the intermediate compound to produce trans-cinnamic acid.

In a third embodiment, a thermally cleavable polymer includes a plurality of CBDA monomers and a plurality of linking monomers polymerizing the CBDA monomers.

In a forth embodiment, a polymer is made by polymerizing cyclobutane diacid (CBDA) monomers with a linker through a condensation reaction and forming a thermally cleavable polymer having a plurality of CBDA monomers linked with a linker.

BRIEF DESCRIPTION OF THE DRAWINGS

FIGS. 10-13 show powder X-ray diffraction of the produced CBDA-1 polymers.

DETAILED DESCRIPTION

A method of making a thermally degradable polymer from cyclobutane-1,3-diacid (CBDA) is disclosed. Two types of CBDA monomers are contemplated in synthesis of thermally cleavable polymers: (1α,2α,3β,4β)-2,4-diphenyl-cyclobutane-1,3-dicarboxylic acid (CBDA-1) and rel-(1R, 2S,3R,4S)-3,4-diphenylcyclobutane-1,2-dicarboxylic acid (CBDA-4). A unique cyclobutane-containing thermoset (CBTS-4) is made from CBDA-4 building blocks while maintaining degradability at high temperatures, allowing for easier recycling of the thermoset. The degraded thermoset intermediary, glycerol cinnamate, confirms the thermally cleavable nature of this thermoset. Similarly, CBDA-1 monomers have the potential to be used to synthesize thermally cleavable polymers.

CBDA-4 Thermally Cleavable Polymers

Figure 1:
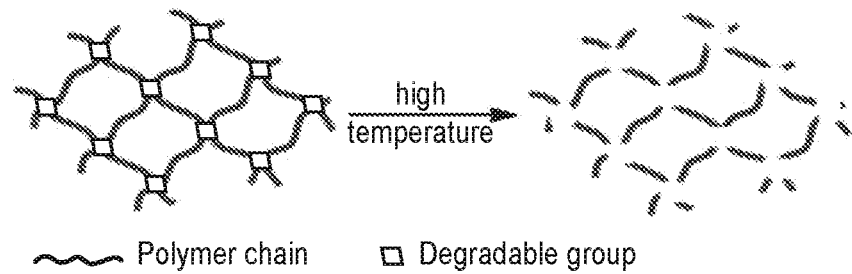
FIG. 1 is a schematic drawing of a thermoset with a built-in thermally degradable group.

FIG. 1 is a schematic drawing of a thermoset polymer with a built-in thermally degradable group breaking down at high temperature. The thermoset polymer, CBTS-4, in FIG. 1 is cross-linked with CBDA-4 building blocks, which creates a potential recyclability, discussed in detail with regards to FIG. 2. CBDA-4 is thermally degradable at high temperatures. Thus, because CBDA-4 is used as a key building block in CBTS-4, the CBDA-4 is also the degradable group allowing for recycling of the CBTS-4 thermoset.

When the thermoset CBTS-4 is degraded, it produces an intermediate, glycerol cinnamate, discussed in detailed with reference to FIGS. 5-7.

Figure 2:
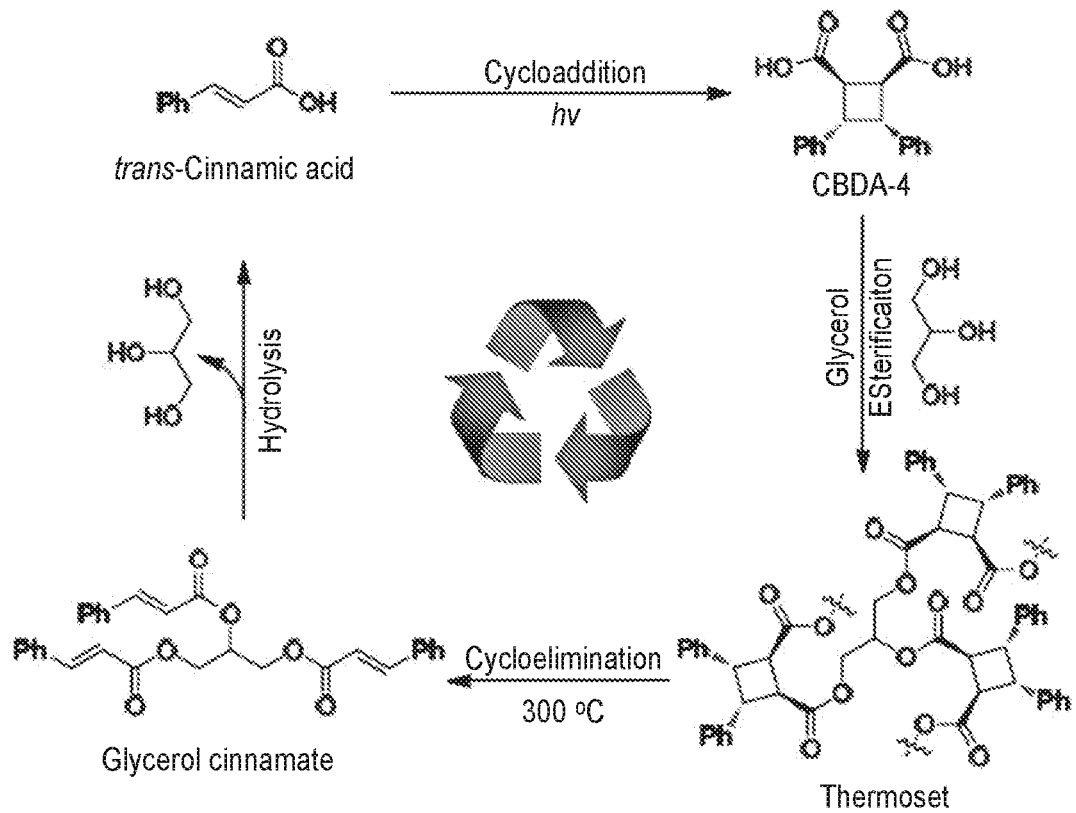
FIG. 2 is a flow chart depicting a method of making a thermoset with a thermally degradable group using rel-(1R, 2S,3R,4S)-3,4-diphenylcyclobutane-1,2-dicarboxylic acid (CBDA-4).

FIG. 2 is a flow chart depicting the synthesis and degradation of thermoset CBTS-4 with a thermally degradable group using CBDA-4. From left to right, the flow chart depicts trans-cinnamic acid starting material, β-trans-cinnamic acid, CBDA-4 building block, cross-linker glycerol, and the CBTS-4 thermoset, ending with the degraded key intermediate glycerol cinnamate.

Before synthesis of thermoset CBTS-4, CBDA-4 building blocks should be obtained. A method of synthesis of CBDA-4 building blocks is discussed in U.S. Patent Appln. No. 62/775,275, which is incorporated herein by reference in its entirety. In this method, trans-cinnamic acid is melted to produce β-trans-cinnamic acid packing, and then irradiated to induce photodimerization and produce CBDA-4.

First, commercially obtained trans-cinnamic acid is melted (trans-cinnamic acid can be purchased from Alfa Aesar, Acros Organic, Matheson Coleman & Bell Manufacturing Chemists, or other sources). trans-cinnamic acid can be melted, for example, in an oven. The melting point of trans-cinnamic acid, as shown in Table 1, is about 133 degrees Celsius.

Next, trans-cinnamic acid is dissolved in an organic solvent to form a trans-cinnamic acid solution. The organic solvent can be, for example, dimethylformamide (DMF), dimethyl sulfoxide (DMSO), diethylformamide (DEF), N-methyl-2-pyrrolidone (NMP), tetrahydrofuran (THF), acetonitrile, and alcohols. The resulting solution can be heated, sonicated, or stirred by other methods to fully dissolve trans-cinnamic acid in the organic solvent. After mixing, the solution should be filtered using techniques known in the art to remove any possible α-trans-cinnamic acid crystal seed.

Subsequently, the trans-cinnamic acid solution is mixed into a poor solvent with temperature near 0° C., for example, ice water. Alternatively, a poor solvent (or mixed poor solvent) with low solubility for trans-cinnamic acid such as brine, hexane, cyclohexane, pentane, heptane, or petroleum ether at a temperature below 15° C. can be used. The trans-cinnamic acid can be mixed into the solvent with stirring to create a slurry. The trans-cinnamic acid solution should be precisely added to the poor solvent. The trans-cinnamic acid solution can be added to the poor solvent in a dropwise method or by injection, for example, with a syringe or any other injection device known in the art. The trans-cinnamic acid in β form is precipitated out as a white powder suspended in ice water.

The slurry is irradiated with blacklight to form cis-cyclobutane-1,2-dicarboxylic acid (CBDA-4). head-to-head packed, β-trans-cinnamic acid is photodimerized to CBDA-4. CBDA-4 is then precipitated and filtered out.

CBDA-4 is then polymerized with a linker molecule. The linker molecule contains a central non-reactive R group, and two to four X groups attached to the R group. The X groups are reactive with CBDA-4 to induce polymerization. The non-reactive R group can be, for example, an aliphatic chain, such as methylene, ethylene, propylene, butylene, pentylene, hexylene, heptylene, octylene with a general structure of —(CH$_2$)—, where n is an integer. Alternatively, the R group can be an aliphatic heterochain (such as —CH$_2$CH$_2$OCH$_2$CH$_2$—, —CH$_2$CH$_2$OCH$_2$CH$_2$OCH$_2$CH$_2$—, —CH$_2$CH$_2$SCH$_2$CH$_2$—, —CH$_2$CH$_2$NHCH$_2$CH$_2$—), a branched aliphatic chain or heterochain (such as —CH(CH$_3$)CH$_2$—, —CH(CH$_3$)CH$_2$CH$_2$—, —CH$_2$CH(CH$_3$)CH$_2$—, —CH(CH$_2$CH$_2$CH$_3$)CH$_2$—, CH(CH$_3$)CH$_2$C(CH$_3$)$_2$—, —CH$_2$CH(OH)CH$_2$—, —CH$_2$CH(NH$_2$)CH$_2$—), a molecule containing substituted or unsubstituted aliphatic rings (such as —C$_6$H$_{10}$—, —CH$_2$(C$_4$H$_6$)CH$_2$—, —CH(C(CH$_3$)$_2$)$_2$CH— (or 2,2,4,4-tetramethyl-1,3-cyclobutanyl)), a molecule containing substituted or unsubstituted aromatic rings (such as —C$_6$H$_4$—, —CH$_2$(C$_6$H$_4$)CH$_2$—, —CH$_2$(C$_4$H$_2$O)CH$_2$— (or furan-2,5-dimethylene), —CH$_2$(C$_4$H$_2$S)CH$_2$— (or thiophene-2,5-dimethylene), —CH$_2$(C$_4$H$_2$NH)CH$_2$— (or pyrrole-2,5-dimethylene)), a substituted or unsubstituted heterocyclic ring (such as dioxane, tetrahydrofuran, pyridine, furan, or thiophene), or combinations of any of the above (such as —CH$_2$C$_6$H$_4$CH$_2$OCH$_2$CH$_2$—).

The reactive X groups on the linker molecule can be all the same, all different, or a combination thereof. Each X group is reactive with the CBDA diacid groups, allowing polymerization when the linker molecule and CBDA monomer are combined. Suitable X groups include nitrogen-containing functional groups (including, but not limited to, amine, imine, oxime, imide, cyanates, isocyanate, azide, azo), oxygen-containing functional groups (including, but not limit to, hydroxyl, carboxyl, carboxylate, and epoxide-containing groups), halogens, carbon containing functional groups (including, but not limit to, alkyne), sulfur-containing functional groups (including, but not limited to, thiol or thiocyanate), boron-containing functional groups, phosphorus-containing functional groups, metals and metal cations (including, but not limit to, zinc, copper, calcium, magnesium, aluminum, iron, manganese, nickel, lithium, sodium, or potassium ions), and combinations of any of the above (such as chloropyridinyl, vanillyl, —CHBrCH$_2$N=C=O, or —CHN$_2$—, isosorbide, starch, glucose, cyclodextrin, or amino acid).

In one example, CBDA-4 is polymerized with a glycerol linker through esterification reaction to form the thermoset CBTS-4. The produced CBDA-4 is added to an organic solvent, such as anhydrous acetonitrile, chloroform, dichloromethane, toluene, and acetone. Condensation catalysts such as such as 1,2-dichloroethane (EDC), 4-dimethylaminopyridine (DMAP), titanium isopropoxide, and tin (II) ethylhexanoate can be used to process the esterification. The solution is mixed through stirring or other methods accepted in the art. A glycerol solution is then added to the CBDA-4 solution dropwise. The glycerol solution can be, for example, glycerol in acetonitrile or other appropriate organic solvent such as anhydrous chloroform, dichloromethane, toluene, and acetone. The esterification may alternatively be carried out under solvent-free conditions. This mixture is mixed together, for example through stirring for a period of 0.1 hour-180 hours in a temperature range of 15° C. to 400° C.

The CBDA-4/glycerol mixture is then mixed into water, methanol, or ethanol and precipitated out. The precipitate is filtered with methods accepted in the art, and subsequently dried in a vacuum to remove any possible solvent(s) tripped in the polymer. After filtering and drying, the thermoset CBTS-4 is obtained as a white powder.

After production of CBTS-4, it was degraded for thermocleavability analysis. To degrade the CBTS-4, test can be performed in a pre-heated device, such as sand bath, oil bath, or oven in a temperature range of 120 to 500 degree Celsius.

Figure 3:
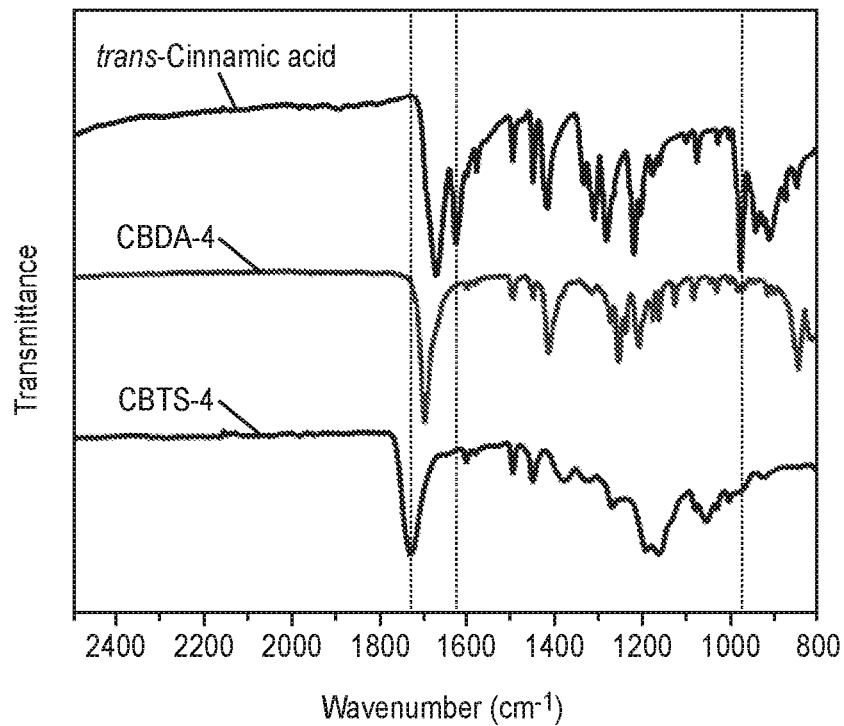
FIG. 3 is an FT-IR spectrum of trans-cinnamic acid, CBDA-4, and the thermoset.

FIG. 3 show FT-IR spectra of trans-cinnamic acid, CBDA-4, and the thermoset on the same axes. In the initial trans-cinnamic acid spectrum, two peaks at 1627 cm$^{-1}$ (C=C stretching) and 976 cm$^{-1}$ (C=C—H out of plane behind) correspond to the double bond. These peaks vanish from the spectrum after photocycloaddition reaction to CBDA-4. Another peak at 1671 cm$^{-1}$ (C=O stretching) in the trans-cinnamic acid spectrum shifted to 1697 cm$^{-1}$ on the CBDA-4 spectrum, indicating deconjugation of the carboxylic group from the rest of the molecule, due to disappearance of the alkene group during photodimerization.

After esterification between CBDA-4 and glycerol, the band at 1697 cm$^{-1}$ (C=O stretching) on the CBDA-4 spectrum moved to 1729 cm$^{-1}$ with a shoulder at 1737 cm$^{-1}$ in the spectrum of the thermoset CBTS-4. This is due to the middle oxyl group on glycerol moiety is different than the oxyl groups on the two wings of glycerol moiety.

Figure 4A:
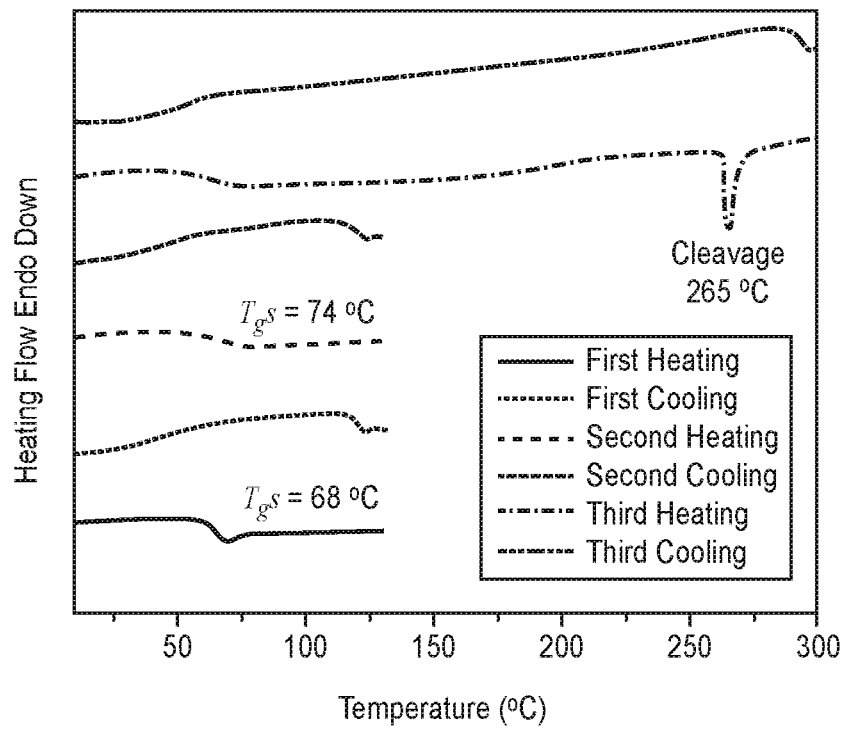
FIGS. 4A-4C show DSC and TGA curves for the thermoset CBTS-4 and a degraded intermediate, glycerol cinnamate.

The produced thermoset CBTS-4 was studied for thermocleavbility under differential scanning calorimetry (DSC) and thermogravimetric analysis (TGA). DSC and TGA tests show the thermal properties of the polymer, such as the glass transition temperature and thermostability. FIG. 4A shows DSC data. Three heating-cooling cycles were applied to CBTS-4 samples during DSC testing. DSC curves were recorded from 10° C. to 130° C. at first and second heating-cooling cycles. For the third heating-cooling cycle, DSC was recorded from 10° C. to 300° C. All heating-cooling cycles were recorded with a heating rate of 20° C. per minute under nitrogen atmosphere.

The first and second heating-cooling cycles provided the glass transition temperature ($T_g$) of the synthesized thermoset, which was 68° C. during the first heating-cooling cycle. The second $T_g$ (the glass transition temperature of the thermoset in the second heating-cooling cycle) was observed at 74° C., which can be attributed to an annealing process happening during the first heating-cooling cycle. The third heating-cooling cycle was used to test the thermal behavior of CBTS-4 at high temperatures. In the third heating-cooling cycle, the third $T_g$ was nearly identical to the second $T_g$. An endothermal peak was observed at 265° C. According to the thermostability of CBDA-4 building blocks, this peak may correspond to the thermocleavage of the thermoset CBTS-4.

Figure 4B:
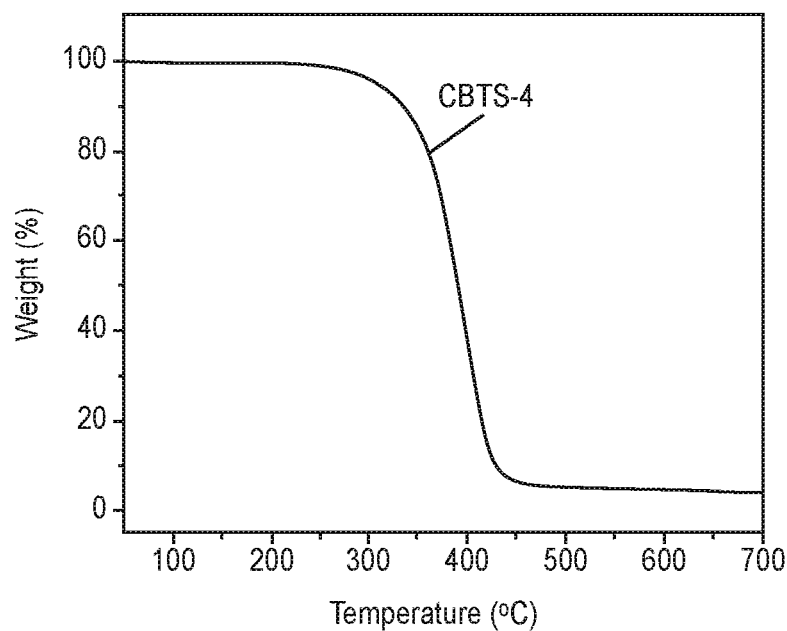

FIG. 4B shows TGA analysis of CBTS-4. TGA showed a 5% weight loss at 300° C. and the residue weight was 4% at 600° C. The TGA result indicated the high thermostability of CBTS, which can lead to a variety of applications of the polymers.

Figure 4C:
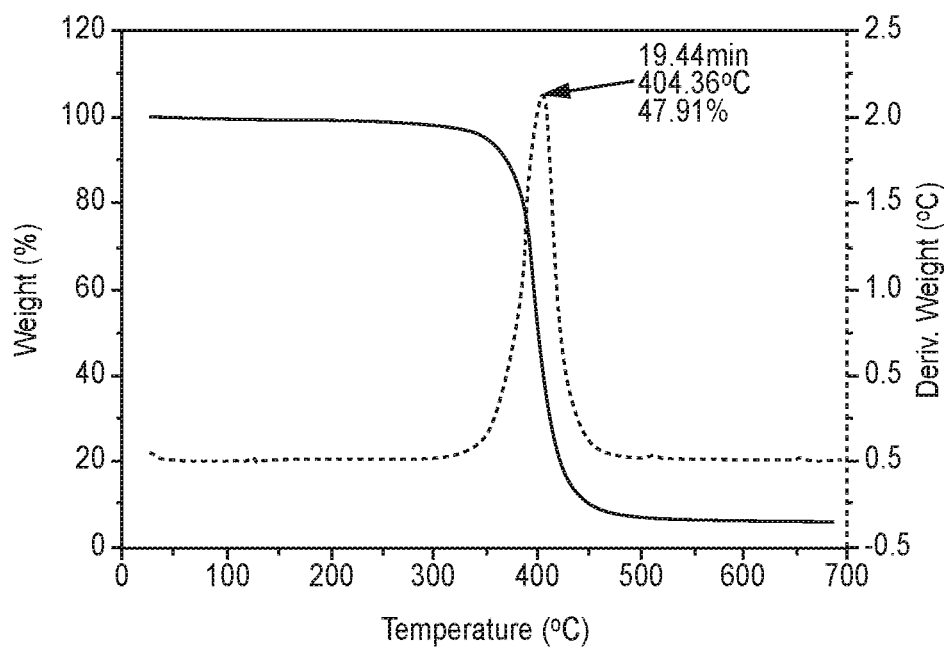

Further analysis of CBTS-4 was done with a powder sample of CBTS-4 purged with argon and heated at high temperatures. A key intermediate compound, glycerol cinnamate, was isolated through column chromatography. FIG. 4C shows TGA and DSC curves for the degraded intermediate, glycerol cinnamate. The TGA result indicates the high thermostability of glycerol cinnamate, which can be further hydrolyzed to the CBDA-4 starting materials cinnamic acid and glycerol.

Both CBTS-4 and the glycerol cinnamate intermediate were studied with FT-IR, NMR, HRMS, and X-ray diffraction, discussed with reference to FIGS. 5-7 below.

Figure 5A:
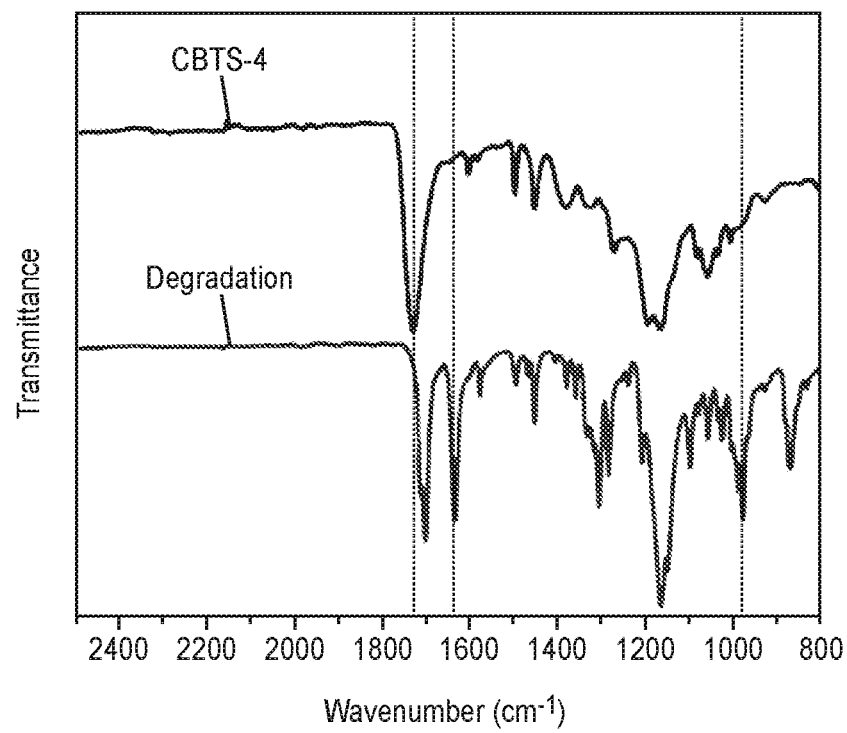
FIGS. 5A-5B show FT-IR spectra of the thermoset and glycerol cinnamate.
Figure 5B:
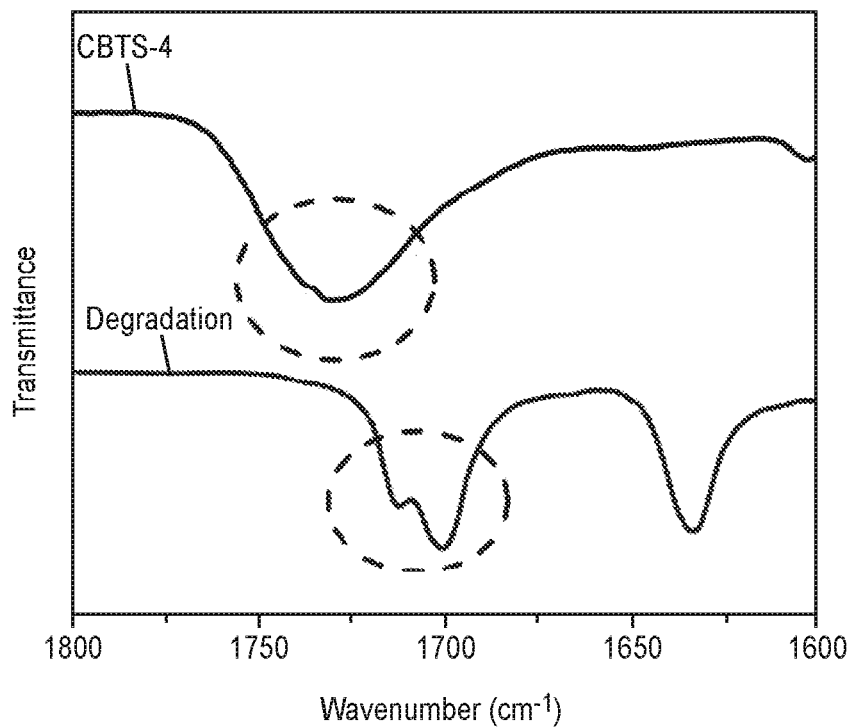

FIGS. 5A-5B show FT-IR spectra of the thermoset CBTS-4 and a degraded intermediate, glycerol cinnamate, respectively. The spectrum for CBTS-4 is discussed with reference to FIG. 3. The spectrum for glycerol cinnamate shows two new bands at 1635 cm$^{-1}$ and 971 cm$^{-1}$ after degradation. The two new bands are similar to C=C stretching and C=C—H out of plane bending in the spectrum for trans-cinnamic acid (FIG. 3, 1627 cm$^{-1}$ C=C stretching, and 976 cm$^{-1}$ C=C—H out of plane bending). Additionally, in the glycerol cinnamate spectrum, peaks at 1714 cm$^{-1}$ and 1701 cm$^{-1}$ show two carbonyl groups with different chemical environment, similar to the two bands of thermoset CBTS-4.

Figure 6A:
FIG. 6 shows proton NMR spectra of trans-cinnamic acid, CBDA-4, and glycerol cinnamate.
Figure 6B:
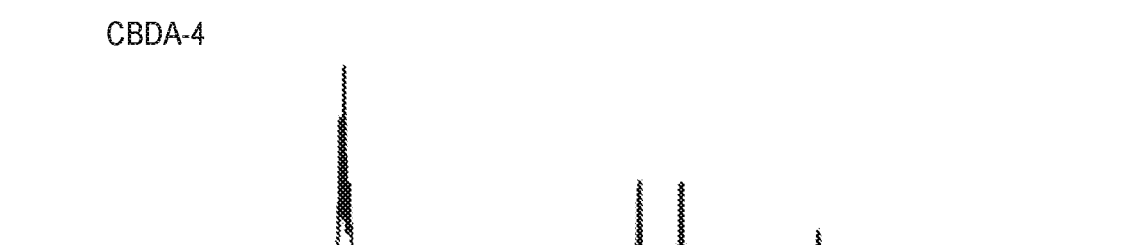
Figure 6C:
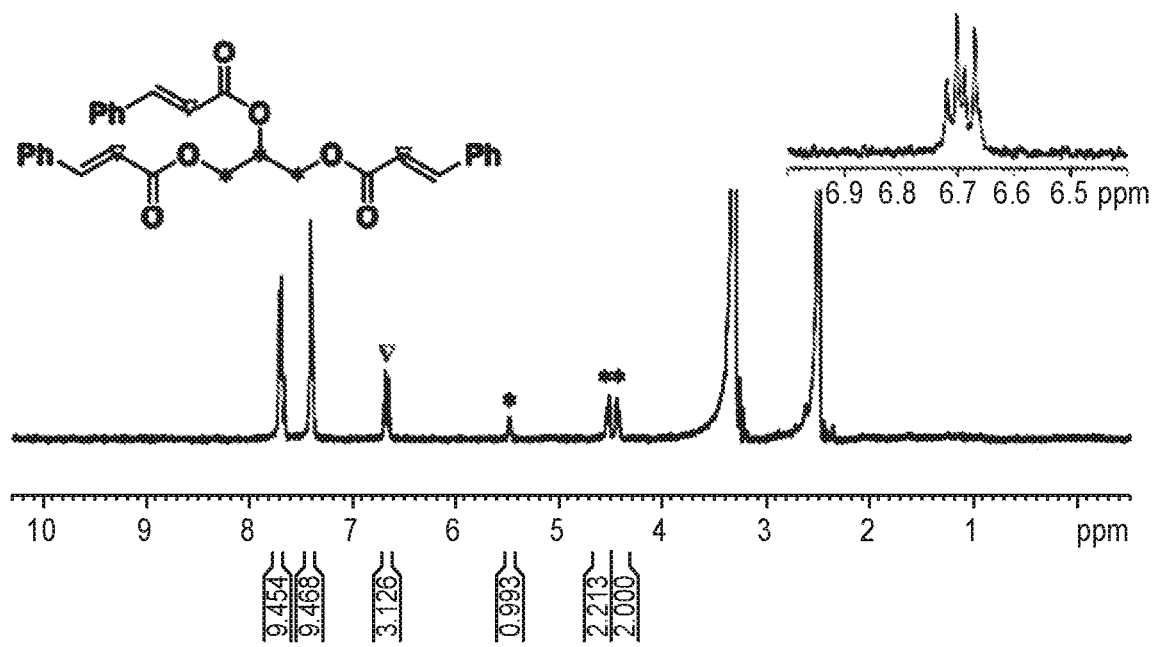

FIGS. 6A-6C show proton $^1$H NMR spectra of trans-cinnamic acid, CBDA-4, and glycerol cinnamate, respectively. The $^1$H NMR spectrum of CBDA-4 has two sp$^3$C peaks from the cyclobutane ring (δ: d, 4.22 ppm, J=4.5 Hz and d, 3.83 ppm, J=4.5 Hz). By comparison, trans-cinnamic acid contains two C=C bond peaks.

After degradation of CBTS-4, the spectrum for glycerol cinnamate shows two pairs of new C=C bond peaks corresponding to the ones next to the carbonyl groups at 6.67 (d, J=16 Hz) and 6.69 (J=16 Hz) ppm. This is shown in the insert of FIG. 6C. The integration of the peak at 6.67 ppm was twice the one at 6.69 ppm, indicating two equal double bonds and one unequal double bond.

In the intermediate glycerol cinnamate spectrum, the peaks at 4.44 and 4.53 ppm correspond to the —CH$_2$—O— in the glycerol moiety. The peak at 5.50 ppm corresponds to the —CH—O— group. Meanwhile, the three protons of the Ph-CH=CH— and three phenyl groups appear between 7 and 8 ppm. Thus, the intermediate glycerol is cinnamate. HRMS (found at 505.1701) was consistent with the molecular weight of glycerol cinnamate (calculated from [C$_{30}$H$_{26}$O$_6$Na]$^+$ 505.1627).

Figure 7A:
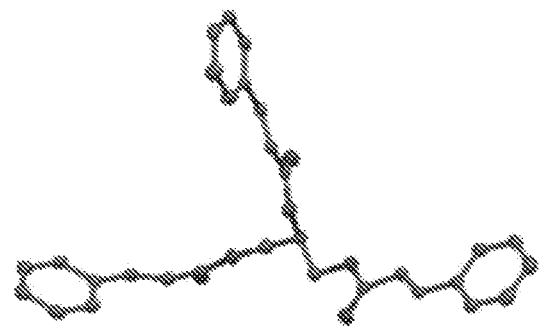
FIGS. 7A-7B show crystal structures of glycerol cinnamate.
Figure 7B:
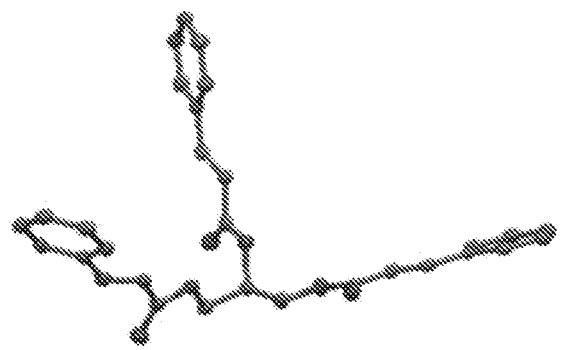

FIGS. 7A-7B show crystal structures of glycerol cinnamate. FIG. 7A shows the top view and FIG. 7B shows the side view of the X-ray structures of glycerol cinnamate. High quality single crystals of the degraded intermediate, glycerol cinnamate, were yielded from DMF solution. The crystal data was collected at 100 K by single crystal X-ray diffraction, and FIGS. 7A-7B represent 50% electron density (hydrogens are omitted for clarity). The glycerol cinnamate adopts a cone shape conformation in the crystal. Along the c axis, the repeating distance was 5.64 Å. Further X-ray crystal structure of glycerol cinnamate is shown below in Table 1.

TABLE 1

| Crystal | Glycerol Cinnamate |
| --- | --- |
| Formula | C$_{30}$H$_{26}$O$_6$ |
| FW | 482.51 |
| Crystal size [mm] | 0.25 × 0.04 × 0.03 |
| Crystal system | Orthorhombic |
| Space group | Pna2$_1$ |
| a (Å) | 14.6141(4) |
| b (Å) | 29.7385(10) |
| c (Å) | 5.6446(2) |
| α (°) | 90 |
| β (°) | 90 |
| γ (°) | 90 |
| V (Å$^3$) | 2453.15(14) |
| Temp. (K) | 100 |
| Z | 4 |
| ρcalc (g · cm$^{-3}$) | 1.306 |
| μ (mm$^{-1}$) | 0.740 |
| Radiation type | MoKα (λ = 0.71073) |
| F(000) | 1016.0 |
| Reflections collected | 9222 |
| Independent reflections | 3599 |
| R1/wR2 (I ≥ 2σ) (%) | 3.60/8.10 |
| R1/wR2 (all data) (%) | 4.26/8.52 |

Figure 8:
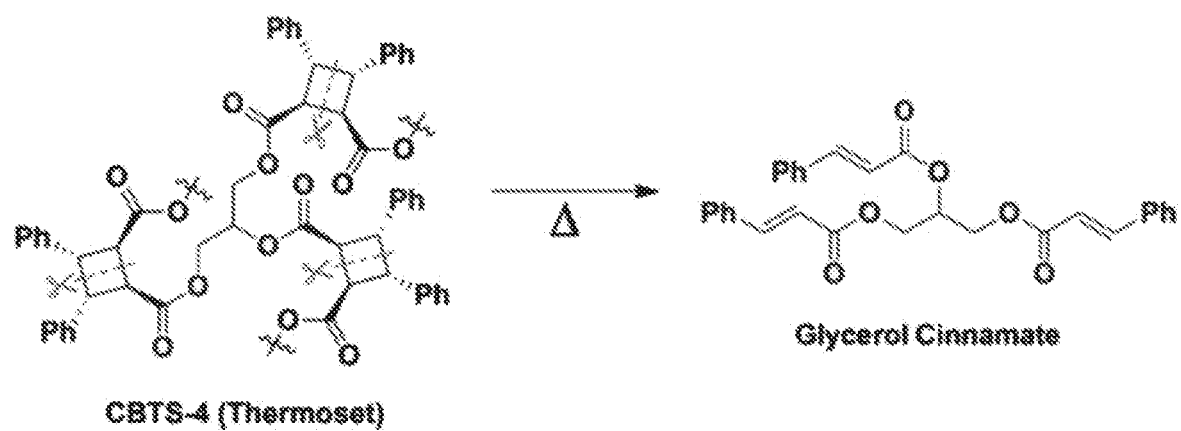
FIG. 8 shows a proposed pathway of the thermoset degradation.

FIG. 8 shows a proposed pathway of the thermoset degradation. The disclosed method includes synthesis of a thermally degradable thermoset from CBDA-4 building blocks, and thermal degradation of that same thermoset. This thermoset is potentially recyclable, as the cyclobutane ring (of the CBDA-4 monomers) serves as a thermally cleavable, degradable group in the backbone of the thermoset. At about 265 degrees Celsius, the cyclobutane ring was split into two double bonds, allowing readable thermoset decomposition to glycerol cinnamate, which can in turn be hydrolyzed back to the initial starting material of trans-cinnamic acid.

CBDA-1 Thermally Cleavable Polymers

A second variant of CBDA, (1α,2α,3β,4β)-2,4-diphenyl-cyclobutane-1,3-dicarboxylic acid (CBDA-1), which is also known as α-truxillic acid, can be used to produce thermally cleavable polyesters. Compared to the other classic diacid building blocks, CBDA-1 represents a unique semi-rigid building block in material synthesis due to the presence of the small aliphatic ring. The synthesis and polymerization of CBDA-4 is described in detail in U.S. Patent Appln. No. 62/527,590, which is incorporated herein by reference in its entirety.

Figure 9:
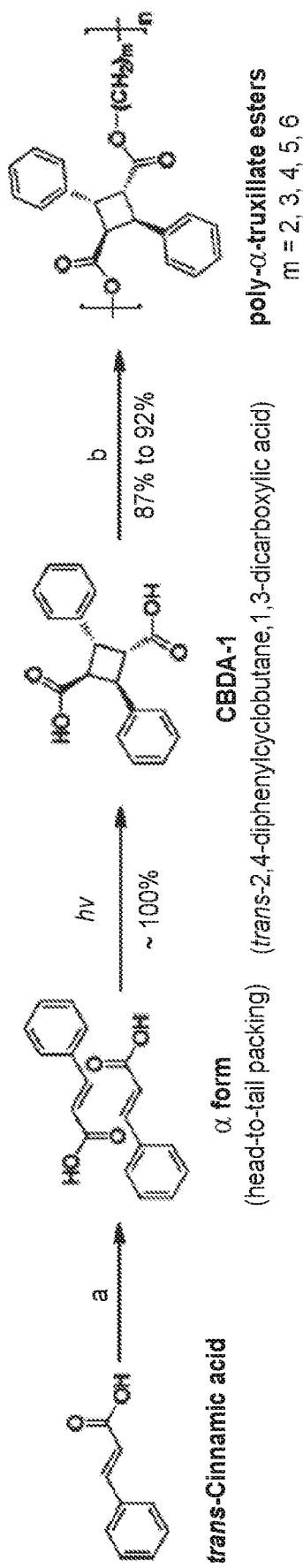
FIG. 9 is a schematic drawing showing the synthesis of CBDA-1 monomers and polymers.
Figure 14:
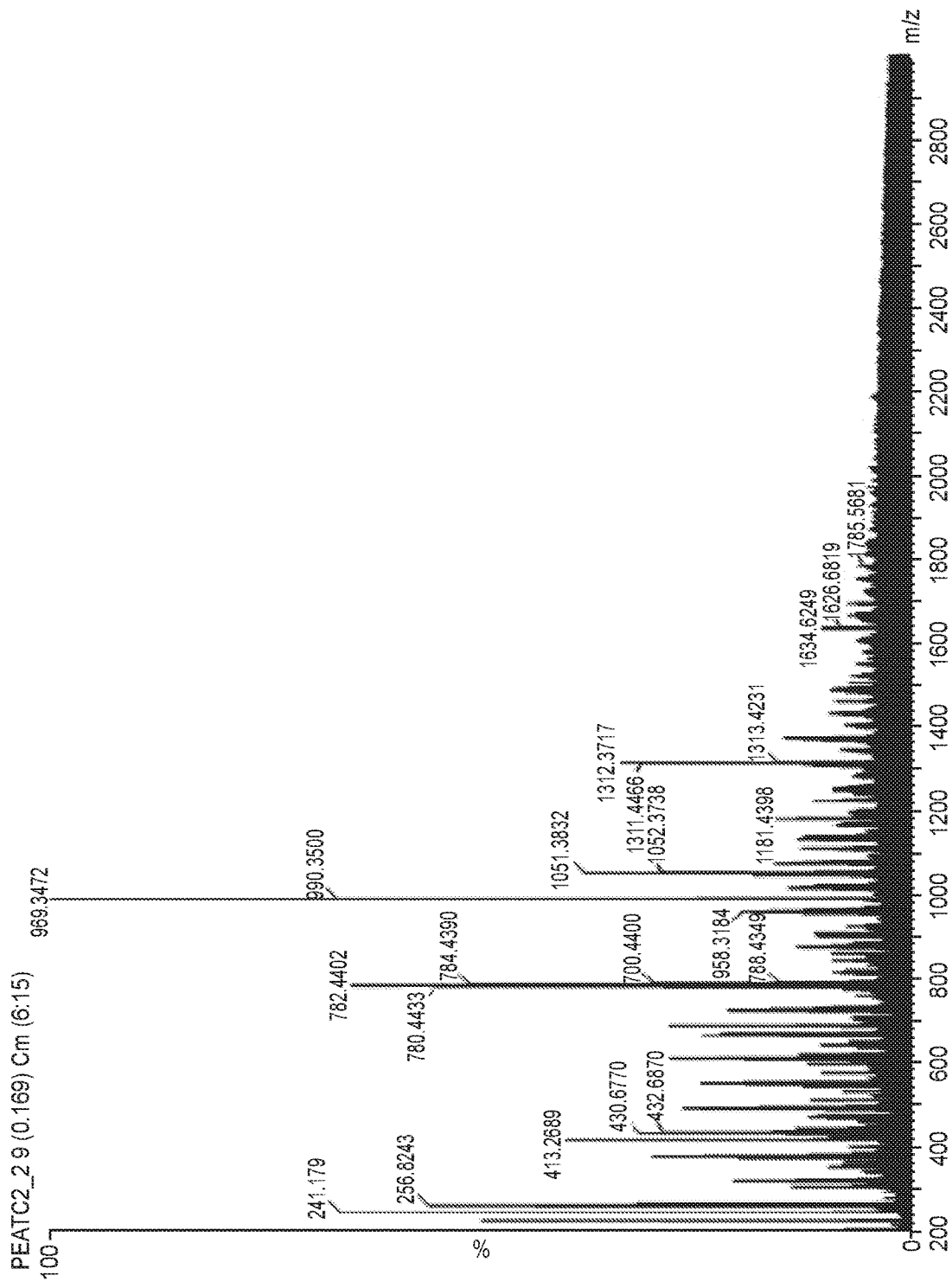
FIGS. 14-17 show mass spectra of the produced CBDA-1 polymers.
Figure 15:
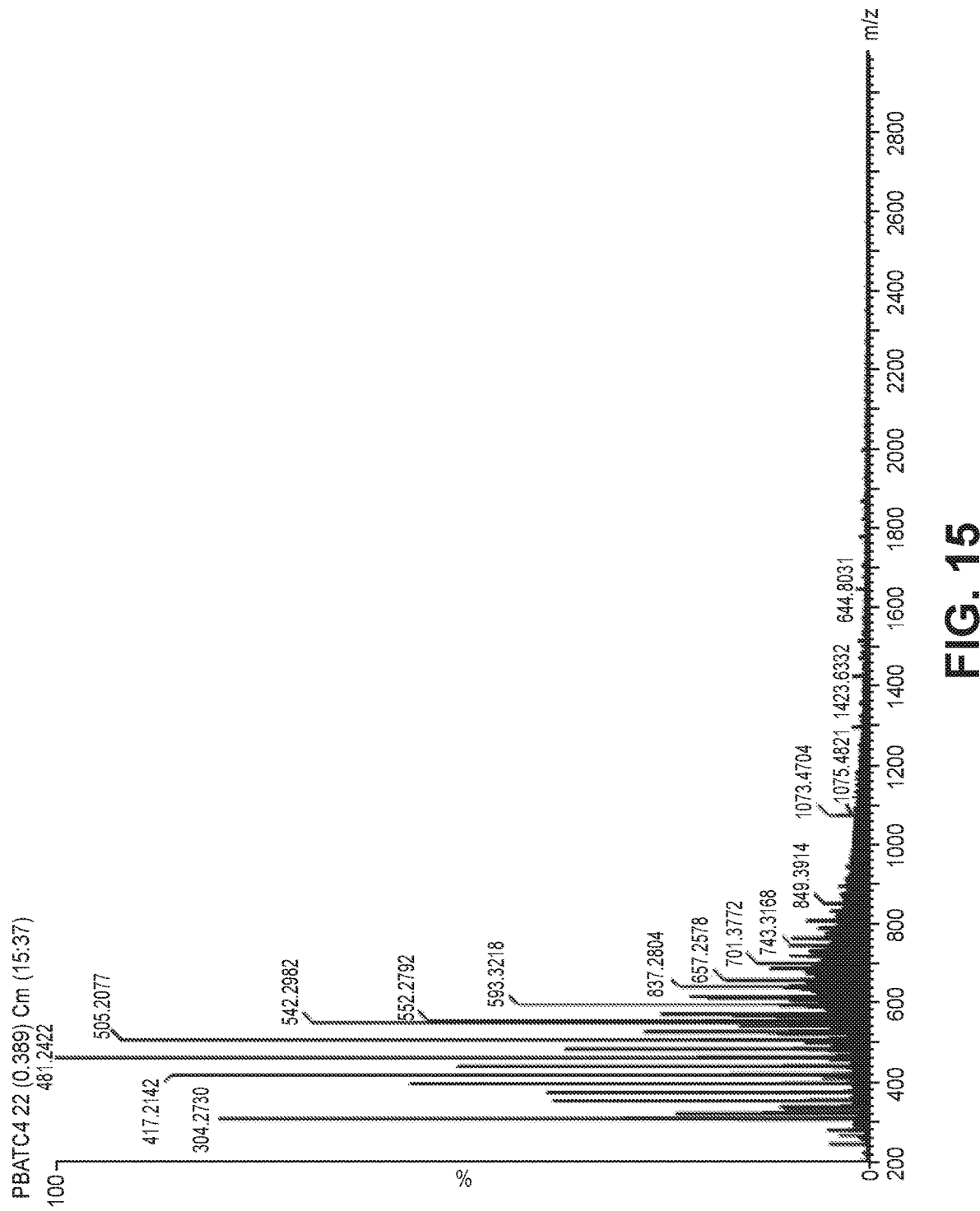
Figure 16:
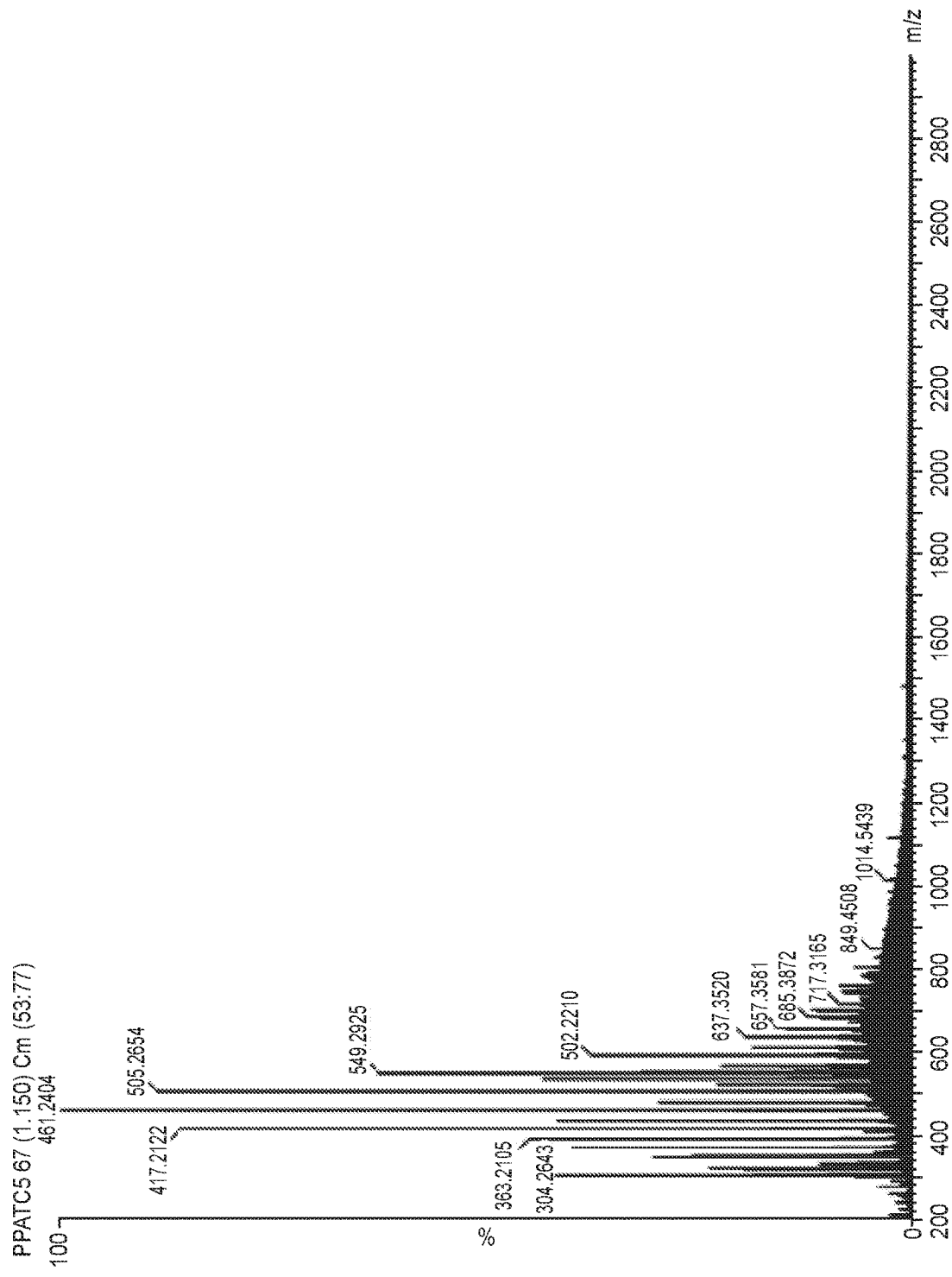
Figure 17:
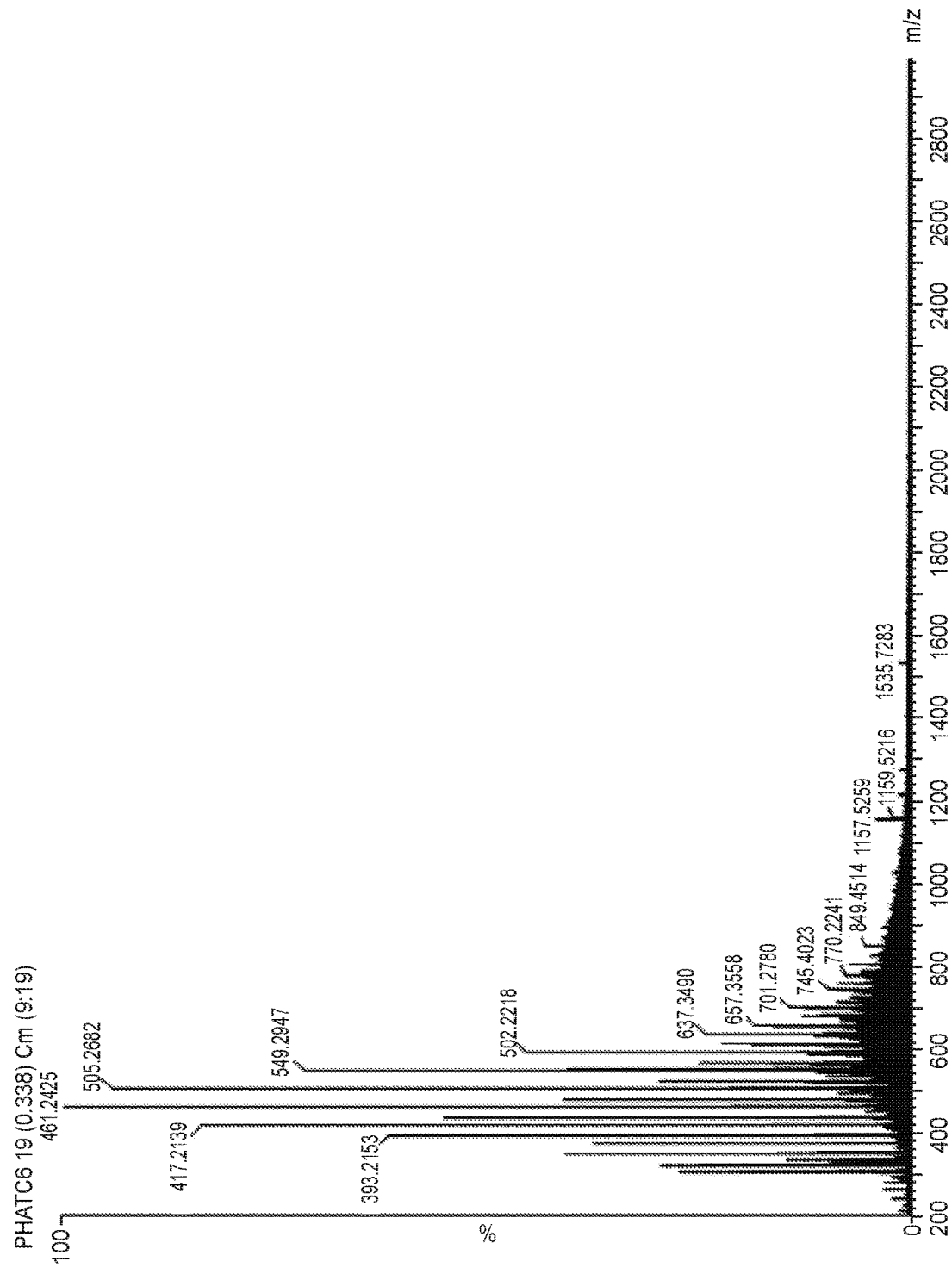
Figure 18:
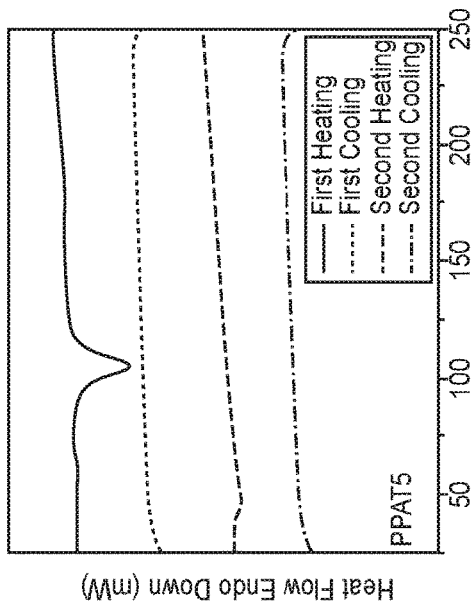
FIGS. 18-21 show thermostability analysis of the produced CBDA-1 polymers.
Figure 19:
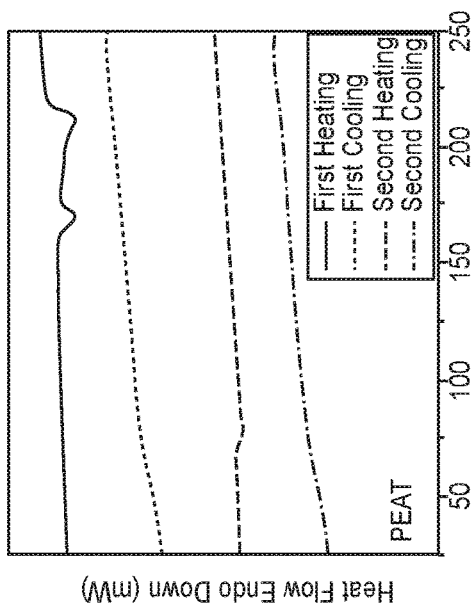
Figure 20:
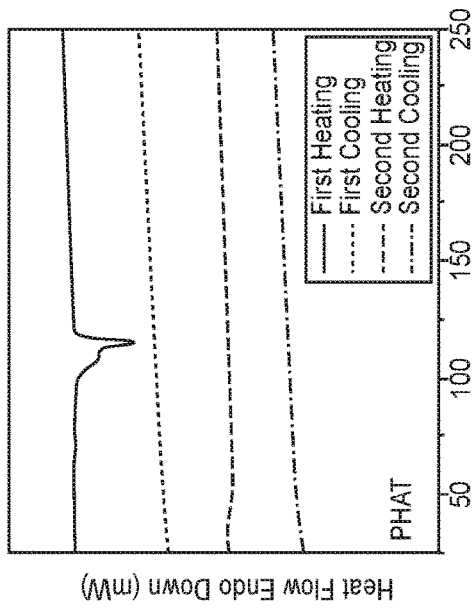
Figure 21:
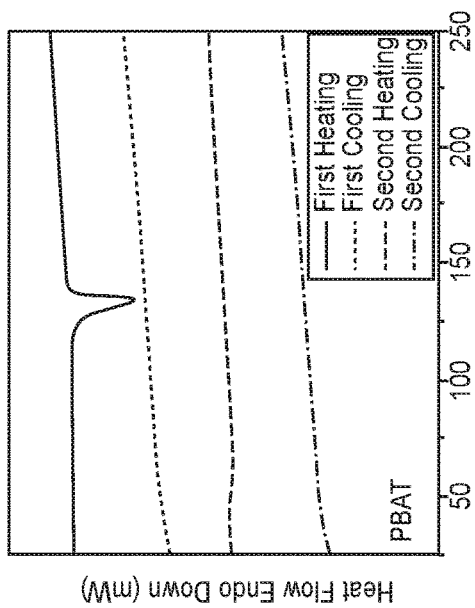

FIG. 9 shows a scheme of synthesizing CBDA-1 molecules and poly-α-truxillate. CBDA-1 can be readily synthesized from commercially available trans-cinnamic acid via photodimerization in the solid-state. This process can be fulfilled in 8 hours in near quantitative yield without side products, allowing CBDA-1 to be used in subsequent steps without further purification.

The efficiency of the solvent-free photoreaction is due to complementary π-π interactions between adjacent trans-cinnamic acid molecules, which are enabled or potentiated by head-to-tail (α-form) packing in the solid state. Phenyl groups, on one end of the molecule, act as weak electron donating groups while carboxylic acid groups, on the opposite end, function as weak electron accepting groups. The end result is that, flat, conjugated trans-cinnamic acid molecules are relatively polar and prefer a head-to-tail packing formation because it is lower in energy.

High quality single crystals of trans-cinnamic acid were obtained in a mixed solvent of ethyl acetate and acetonitrile (1:1). X-ray diffraction analysis confirmed its head-to-tail packing. The head-to-tail packing can be obtained in a variety of solvents, including acetonitrile, acetone, toluene, methanol, tetrahydrofuran (THF), and chloroform showing that the α-form is the dominant packing conformation for trans-cinnamic acid. Moreover, powder X-ray diffraction (PXRD) confirms that the packing of commercial trans-cinnamic acid is the head-to-tail form because its powder pattern is nearly identical to that of the head-to-tail single crystal simulation. Consequently, commercial trans-cinnamic acid powder can be used to produce the building block, CBDA-1, directly without recrystallization. Only one of the five stereoisomers of the [2+2] head-to-tail dimers was produced because solid state photoreaction normally proceeds with minimum movement of atoms.

CBDA-1 is then polymerized with a linker molecule. The linker molecule contains a central non-reactive R group, and two to four X groups attached to the R group. The X groups are reactive with CBDA-1 to induce polymerization. The non-reactive R group can be, for example, an aliphatic chain, such as methylene, ethylene, propylene, butylene, pentylene, hexylene, heptylene, octylene with a general structure of —(CH$_2$)—, where n is an integer. Alternatively, the R group can be an aliphatic heterochain (such as —CH$_2$CH$_2$OCH$_2$CH$_2$—, —CH$_2$CH$_2$OCH$_2$CH$_2$OCH$_2$CH$_2$—, —CH$_2$CH$_2$SCH$_2$CH$_2$—, —CH$_2$CH$_2$NHCH$_2$CH$_2$—), a branched aliphatic chain or heterochain (such as —CH(CH$_3$)CH$_2$—, —CH(CH$_3$)CH$_2$CH$_2$—, —CH$_2$CH(CH$_3$)CH$_2$—, —CH(CH$_2$CH$_2$CH$_3$)CH$_2$—, CH(CH$_3$)CH$_2$C(CH$_3$)$_2$—, —CH$_2$CH(OH)CH$_2$—, —CH$_2$CH(NH$_2$)CH$_2$—), a molecule containing substituted or unsubstituted aliphatic rings (such as —C$_6$H$_{10}$—, —CH$_2$(C$_4$H$_6$)CH$_2$—, —CH(C(CH$_3$)$_2$)$_2$CH— (or 2,2,4,4-tetramethyl-1,3-cyclobutanyl)), a molecule containing substituted or unsubstituted aromatic rings (such as —C$_6$H$_4$—, —CH$_2$(C$_6$H$_4$)CH$_2$—, —CH$_2$(C$_4$H$_2$O)CH$_2$— (or furan-2,5-dimethylene), —CH$_2$(C$_4$H$_2$S)CH$_2$— (or thiophene-2,5-dimethylene), —CH$_2$(C$_4$H$_2$NH)CH$_2$— (or pyrrole-2,5-dimethylene)), a substituted or unsubstituted heterocyclic ring (such as dioxane, tetrahydrofuran, pyridine, furan, or thiophene), or combinations of any of the above (such as —CH$_2$C$_6$H$_4$CH$_2$OCH$_2$CH$_2$).

The reactive X groups on the linker molecule can be all the same, all different, or a combination thereof. Each X group is reactive with the CBDA diacid groups, allowing polymerization when the linker molecule and CBDA monomer are combined. Suitable X groups include nitrogen-containing functional groups (including, but not limited to, amine, imine, oxime, imide, cyanates, isocyanate, azide, azo), oxygen-containing functional groups (including, but not limit to, hydroxyl, carboxyl, carboxylate, and epoxide-containing groups), halogens, carbon containing functional groups (including, but not limit to, alkyne), sulfur-containing functional groups (including, but not limit to, thiol or thiocyanate), boron-containing functional groups, phosphorus-containing functional groups, metals and metal cations (including, but not limit to, zinc, copper, calcium, magnesium, aluminum, iron, manganese, nickel, lithium, sodium, or potassium ions), and combinations of any of the above (such as chloropyridinyl, vanillyl, —CHBrCH$_2$N=C=O, or —CHN$_2$, isosorbide, starch, glucose, cyclodextrin, or amino acid).

In one example, a CBDA-1 polymer, poly-α-truxillate, can be synthesized using a series of linear diols and condensation reactions to polymerize CBDA-1. Five poly-α-truxillate can be produced, poly(ethylene-α-truxillate) (PEAT), poly(propylene-α-truxillate) (PPAT3), poly(1,4-butylene-α-truxillate) (PBAT), poly(1,5-pentylene-α-truxillate) (PPAT), poly(1,6-hexylene-α-truxillate) (PHAT).

FIGS. 10-13 show powder X-ray diffraction of the produced CBDA-1 polyesters. Powder X-ray diffraction patterns of these four poly-α-truxillates showed that they are semi-crystalline as shown in FIGS. 22-25. Two series of peaks were observed in the HRMS spectrum of PEAT as shown in FIG. 6, which was determined by preliminary MALDI-TOF analysis. They have a repeating unit with m/z=322.12 that corresponds with the unit mass of PEAT (C$_{20}$H$_{18}$O$_4$ m/z=322.12). One repeating peak of PEAT is 'm/z=322.12×n+22.99 (Na)' which may indicate that some cycled polyesters exist in the product. For example, 'm/z=322.12×3+22.99=989.35'. Another repeating peak of PEAT is 'm/z=322.12×n+62.04 (end-group)+22.99 (Na)'. This result suggests there are linear polyesters with end-groups HO—(CH$_2$)$_2$— and —OH. For example, 'm/z=322.12×3+62.04+22.99=1051.39'.

FIGS. 14-17 show mass spectra of the produced CBDA-1 polyesters. The MS analysis of PEAT revealed both linear and cycled fragments can potentially be present in PEAT, as shown in FIGS. 26A-26C. This phenomenon of two different repeating peaks in HRMS spectra was also observed in PBAT, PPAT, and PHAT (FIGS. 27-29). Both NMR and HRMS spectra indicated that PEAT was the only compound with a significant number of cycled products (FIGS. 12-16). This is probably because it is difficult to form cycled products when the linker molecules contain long and flexible carbon chains. The maximum molecular weights observed in HRMS spectra indicate six-mers.

FIGS. 18-21 show thermostability analysis of the produced CBDA-1 polyesters. Thermogravimetric analysis (TGA) indicates that the synthesized poly-α-truxillate have excellent thermal stability, which is consistent with its CBDA-1 building block as shown in FIG. 34. DSC was used to analyze the glass transition temperature ($T_g$) of the four polyesters as shown in FIGS. 30-33. The figures show a decreasing trend of the poly-α-truxillate $T_g$s with increasing diol carbon chain length. $T_g$ of PEAT is 81° C. whereas $T_g$ of PPAT is 64° C. This trend of the $T_g$s may be attributed to the increased flexibility of carbon chains with higher carbon numbers. It is easier for the polyester to rotate or twist with long carbon chain. After the first heating and cooling process, the DSC curve showed an obvious decreasing trend of $T_g$s in the second heating process. This phenomenon may be due to the annealing effect of the first heating process. After heating polyesters to 250° C., the polyesters will be scattered and mixed equally that may lead the decreasing $T_g$s.

The polymerization of CBDA monomers to create thermally cleavable polymers can be used to create thermoplastics, thermosets, or elastomers. This facile and scalable innovative method of polymer production and degradation can be used to create recyclable, environmentally friendly polymers with build-in thermally degradable groups.

DISCUSSION OF POSSIBLE EMBODIMENTS

The following are non-exclusive descriptions of possible embodiments of the present invention.

A method of making a polymer includes polymerizing cyclobutane diacid (CBDA) monomers with a linker through a condensation reaction and forming a thermally cleavable polymer having a plurality of CBDA monomers linked with a linker.

The method of the preceding paragraph can optionally include, additionally and/or alternatively, any one or more of the following features, configurations and/or additional components:

The CB DA monomer is (1α,2α,3β,4β)-2,4-diphenylcyclobutane-1,3-dicarboxylic acid (CBDA-1) or rel-(1R,2S,3R,4S)-3,4-diphenylcyclobutane-1,2-dicarboxylic acid (CBDA-4).

The method includes preparing CBDA monomers from trans-cinnamic acid before step a.

Preparing CBDA monomers includes melting trans-cinnamic acid, dissolving trans-cinnamic acid in an organic solvent to create a trans-cinnamic acid solution, creating a slurry from the trans-cinnamic acid solution, and photodimerizaing the slurry to create CBDA-4 monomers.

Creating a slurry comprises adding the trans-cinnamic acid solution to a poor solvent below 15 degrees Celsius.

The poor solvent is selected from the group consisting of water, methanol, and ethanol.

Promoting polymerization can be carried out in a solvent free environment.

Preparing CBDA monomers comprises photodimerization in the solid-state from trans-cinnamic acid to produce CBDA-1 monomers.

The linker includes a non-reactive R group residing in the center of the linker and two or more X groups configured to react with CBDA-4, the two or more X-groups each attached to the R group.

The non-reactive R group is selected from the group consisting of aliphatic chains, aliphatic heterochains, branched aliphatic chains, branched aliphatic heterochains, substituted aliphatic rings, unsubstituted aliphatic rings, substituted aromatic rings, unsubstituted aromatic rings, substituted heterocyclic rings, unsubstituted heterocyclic rings, and combinations thereof.

The two or more X groups are selected from the group consisting of nitrogen-containing functional groups, oxygen-containing functional groups, halogens, carbon containing functional groups, sulfur-containing functional groups, boron-containing functional groups, phosphorus-containing functional groups, metals, metal cations, and combinations thereof.

Polymerizing CBDA monomers includes mixing CBDA into an organic solvent to create a CBDA solution, mixing the linker into an organic solvent to create a linker solution, combining the CBDA solution with the linker solution to create a mixed solution, adding a condensation catalyst to the mixed solution from step c to promote polymerization and precipitating a polymer.

A method of degrading a polymer includes heating the polymer to invoke degradation of cyclobutane rings and produce an intermediate compound and hydrolizing the intermediate compound to produce trans-cinnamic acid.

Heating the polymer is done between 120 and 500 degrees Celsius

Hydrolyzing the intermediate compound comprises mixing the intermediate with a catalyst.

The catalyst is an acid or base selected from the group consisting of potassium hydroxide, sodium hydroxide, sodium hydrochloride, and sulfuric acid.

A thermally cleavable polymer includes a plurality of CBDA monomers and a plurality of linking groups polymerizing the CBDA monomers.

Each of the plurality of linking groups has a general formula of $RX_2$, $RX_3$, or $RX_4$.

A polymer made by polymerizing cyclobutane diacid (CBDA) monomers with a linker through a condensation reaction and forming a thermally cleavable polymer having a plurality of CBDA monomers linked with a linker.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of making a polymer comprising:
   a polymerizing cyclobutane diacid (CBDA) monomers with a linker through a condensation reaction, wherein the CBDA monomer is rel-(1R,2S,3R,4S)-3,4-diphenylcyclobutane-1,2-dicarboxylic acid (CBDA-4) and the linker is glycerol; and
   b. forming a thermally cleavable polymer having a plurality of the CBDA-4 monomers linked with the glycerol linker.

2. The method of claim 1, further comprising preparing CBDA-4 monomers from trans-cinnamic acid before step a.

3. The method of claim 2, wherein preparing CBDA-4 monomers comprises:
   a. melting trans-cinnamic acid;
   b. dissolving trans-cinnamic acid in an organic solvent to create a trans-cinnamic acid solution;
   c. creating a slurry from the trans-cinnamic acid solution; and
   d. photodimerizing the slurry to create CBDA-4 monomers.

4. The method of claim 3, wherein creating a slurry comprises adding the trans-cinnamic acid solution to a poor solvent below 15 degrees Celsius.

5. The method of claim 4, wherein the poor solvent is selected from the group consisting of water, methanol, and ethanol.

6. The method of claim 1, wherein polymerizing CBDA-4 monomers
   a. mixing CBDA-4 into an organic solvent to create a CBDA-4 solution;
   b. mixing the glycerol linker into an organic solvent to create the glycerol linker solution;
   c. combining the CBDA-4 solution with the glycerol linker solution to create a mixed solution;
   d. adding a condensation catalyst to the mixed solution from step c to promote polymerization; and
   e. precipitating a polymer.

7. The method of claim 1, wherein polymerization is carried out under solvent-free conditions.

8. A thermally cleavable polymer obtained by method of claim 1.

9. A method of degrading a polymer, comprising:
   heating the polymer of claim 8 to invoke degradation of cyclobutane rings and produce an intermediate compound; and
   hydrolyzing the intermediate compound to produce trans-cinnamic acid.

10. The method of claim 9, wherein heating the polymer is done between 120 and 500 degrees Celsius.

11. The method of claim 9, wherein hydrolyzing the intermediate compound comprises mixing the intermediate with a catalyst.

12. The method of claim 11, wherein the catalyst is an acid or base selected from the group consisting of potassium hydroxide, sodium hydroxide, sodium hydrochloride, and sulfuric acid.

* * * * *